CARNATION PLANT
Filed May 1, 1973 2 Sheets-Sheet 1
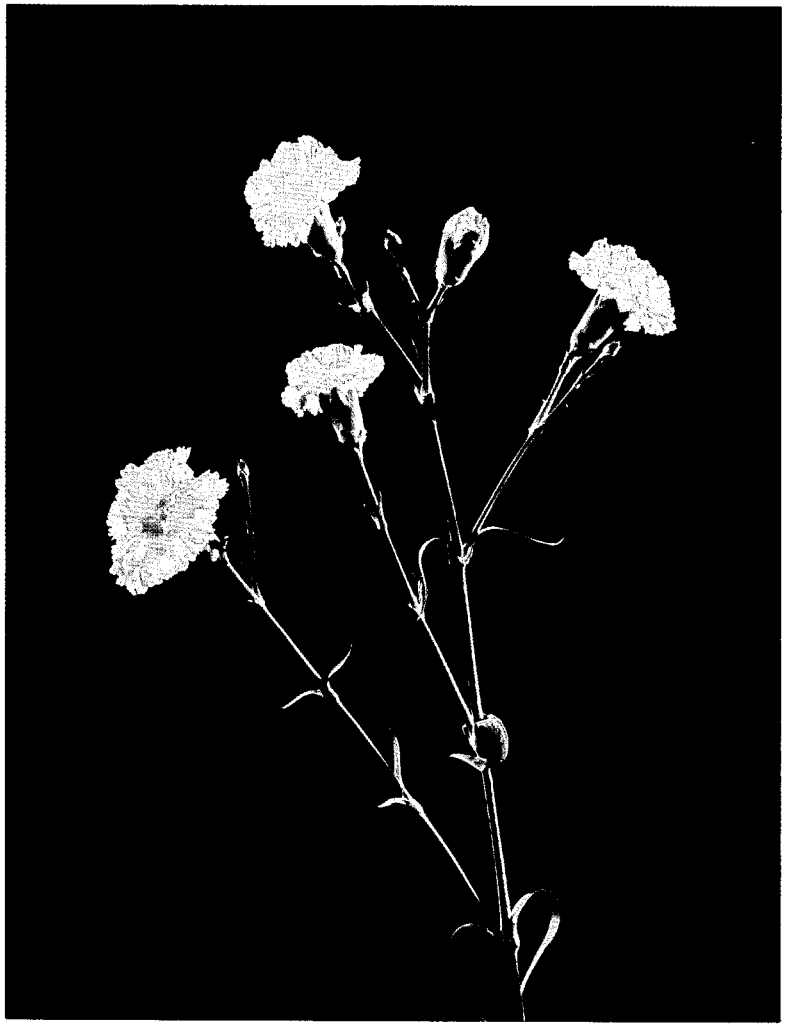

CARNATION PLANT
Filed May 1, 1973 2 Sheets-Sheet 2
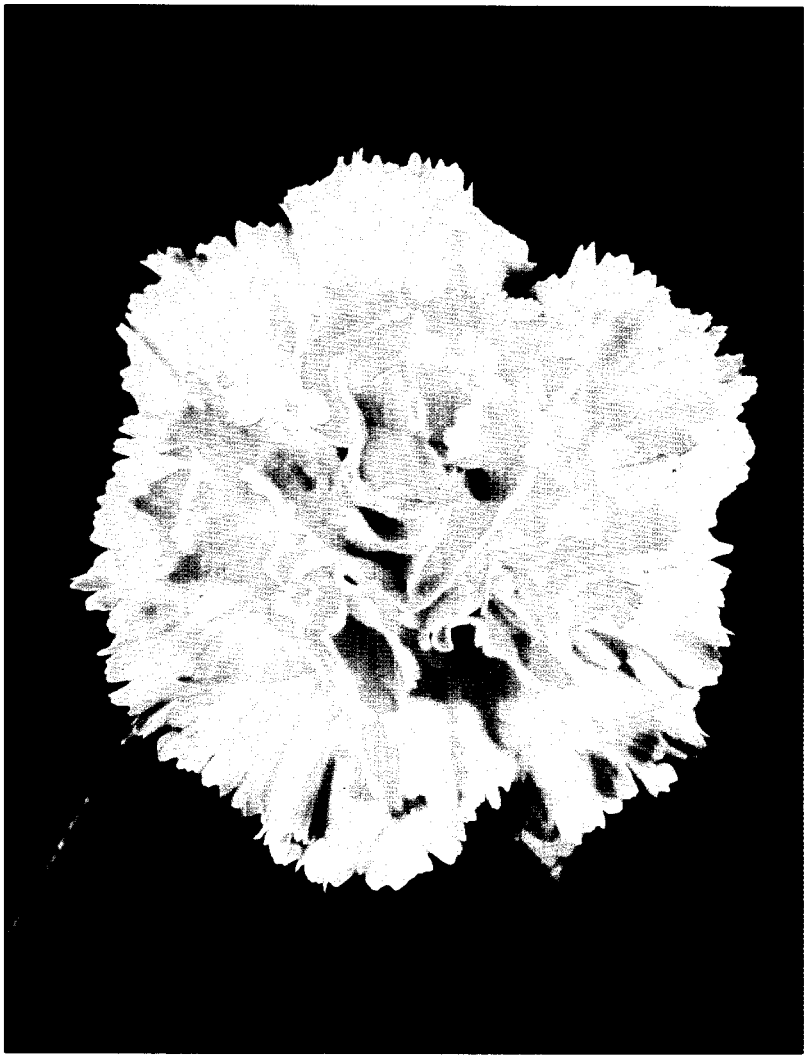

United States Patent Office

Plant Pat. 3,628
Patented Oct. 1, 1974

3,628

CARNATION PLANT

Alexandre Barberet and Henri Blanc, La Londe, France, assignors to Laboratoire de Physiologie Vegetale de La Londe Barberet & Blanc, La Londe, France

Filed May 1, 1973, Ser. No. 356,198
Int. Cl. A01h *5/00*
U.S. Cl. Plt.—70 1 Claim

ABSTRACT OF THE DISCLOSURE

A new variety of carnation plant of the continuously blooming miniature type of the closed calyx or "American" race distinguished by its profuse production of small well formed blossoms of a distinctive red on orange coloring and having an exceptionally long lasting quality as cut flowers.

BACKGROUND OF THE NEW PLANT

This new plant was discovered by us in 1969 among seedlings of a crossing made under our direction between plants selected from breeding stock maintained in our laboratory at La Londe, France. This plant was found to have an original coloring of its flowers as well as favorable characteristics of flower form, vigor and branching and for those reasons was selected by us for propagation and testing. Asexual propagation of this new variety under our direction by cuttings, through successive generations since 1969, has shown the favorable and distinctive characteristics of this plant to be firmly fixed and to hold true from one cultivator to the next.

DESCRIPTION OF THE DRAWINGS

Our new variety of carnation plant is illustrated by the accompanying photographic drawings, in which sheet 1 shows typical inflorescence including buds, partially opened, and full opened blooms; and sheet 2 shows a fully opened flower, the colors being as nearly true as reasonably possible by usual photographic procedures. The color patches applied to sheet 2 show the true Orange and Red Purple colors of the opened flower.

DESCRIPTION OF THE NEW PLANT

The following is a detailed description of this new variety of carnation plant based upon observations made in January 1973 of greenhouse plants set out on July 8, 1972, on raised benches and in a sufficiently moistened calcareous soil. The color designations are according to the R.H.S. Colour Chart published by The Royal Horticultural Society at London, England.

THE PLANT

Origin: Seedling.

Parentage: Seed parent—6P16 (unnamed and unpatented). Pollen parent—112V (unnamed and unpatented). These parent plants are part of our carnation collection maintained for breeding purposes in our laboratories at La Londe, France, and are identified individually and in our permaent records by the above stated numbers.

Classification:

Botanic—Hybrid *Dianthus caryophyllus.*

Commercial—Spray carnation for cut flower production.

Form: Leafy bush of the Sim type.

Height: This plant flowers at an average height of 85 cm. above the soil.

Growth: Vigorous and erect habit with foliage of average density reaching to about 50 cm. from its base in a 6-months old plant.

Branching: Upright, with 4 to 6 flowering stems emerging from around the original cutting at about 7 cm. of its height and rising with an average length of about 80 cm.

Foliage: Quantity—abundant.

*Size of Leaf:* Up to about 12 cm. long and 1.1 cm. wide. The longest leaves appearing between the 8th and 12th joints of the main stems.

*Form of Leaf:* Lanceolate, with entire margins and acuminate apex. Leaves emerge upwardly from the stem and then curve outwardly and downwardly, now and then curled.

*Texture:* Smooth.

*Color:* Bluish Green in overall aspect. Leaves—Greyed Green 189B. Nodes or stem joints—Yellow Green 145C. Stems—Greyed Green 189D.

*Petioles:* None. Leaf is decurrent and amplexicaul.

THE BUD

Calyx: Form—Conical at beginning, becoming ovoid as bud enlarges and then lengthening to become cylindrical and wide-mouthed near the petals.

Size: Average length 2.3 cm.; diameter—1.3 cm. at level of the sepal tips.

Sepals: Shape—Ovate and upstanding with tips curling outward as flower opens and becoming papery and dried.

*Number:* 5 or 6, very rarely 7.

*Striae:* Close together, and the axial stria of each sepal being wider and more visible than the others.

*Color:* Inside—Pale Green. Outside—Pale Green.

Opening: Bud opens rather rapidly.

Color of Flower: When sepals first divide—Red Purple 58B.

Calyx does not split.

Peduncle: Erect and rigid, forming an acute angle with the supporting stem. Average maximum length—20 cm.

THE FLOWER

Blooming Habit: Continuous and profuse. The several levels of flowers open out one after the other without precise order or regularity.

Size of Bloom: Small. Average diameter and depth 5.2 cm. x 2.4 cm.

Borne: Singly, in spray arrangement of flowering branches and floral stems.

Shape: High centered. Shape does not change with flower maturity.

Petalage: About 40 in number, with more-or-less imbricate arrangement of 12 guard petals (sometimes 11) and two rows of center petals. The first row having 12 to 17 petals; and the second row having about one dozen petals, often joined with the petaloids and more-or-less undeveloped stamens.

*Form of Petals*: Fan-shaped and symmetrical with small toothed or serrated and somewhat puckered margins.

*Color*: In general, the background and central portion of the petal blade is of a uniform more-or-less rosy orange color with splotches and short streaks of cyclamen rose over the orange background at the end portion and on the margins of the petal.

The coloring of the flower petals is as follows:

| | Upper side | Reverse side |
|---|---|---|
| Young flower | | |
| Background | Orange 29B | Orange 29C. |
| Streaks-splotches | Red Purple 57B | Red Purple 58B. |
| Fully open flower | | |
| Background | Orange 29C | Orange 29D. |
| Streaks-splotches | Red Purple 58B | Red Purple 58C. |

*Appearance*: Satiny.
*Texture*: Soft.
Petaloids: 8, more-or-less.
*Size*: Half the size of the petals.
*Color*: Same as the petals.
Peduncle: Straight and rigid.
Persistence: Flowers hang on and dry.
Fragrance: Faintly fragrant.
Disease Resistance: Very good to the current diseases of carnations in Southern France.
Lasting Quality:
On plant—20 days
As cut flowers—15 to 20 days

REPRODUCTIVE ORGANS

Stamens:
*Anthers*: About 12 in number, some complete and the others more-or-less undeveloped on their filaments.
*Filaments*: Variable in length, whitish in color and becoming rose colored next to the anthers upon aging.
*Pollen*: Yellowish in color.
Pistils:
Styles—Two in number, rose colored on outer side and papilla on the inner side instead of at the crest.
Length—Average, 3.5 cm. when ripened.
Stigmas: White and reddish when ripe.

Ovaries: Cone shaped. Whitish on the bottom half and light green on the upper half. Yellow-brown where the styles attach.

FRUIT

The fruit is pear-shaped, fertile in the summertime and green and ochreous in color at maturity.

This new variety of carnation plant is particularly distinguished by its exceptionally attractive small and perfectly formed flowers carried by a well formed and entire calyx. The flower is without the central depression so often appearing in other varieties and its fringed petals are bordered by splashes and streaks of intense cyclamen rose on orange color which provides a lively and pleasing appearance. The plant is of average growth habit for varieties of this kind and its flowering stems are long and strong producing well branched inflorescence having many flowers on rigid peduncles of average length.

This plant has a normal precocity with a good aptitude for reflowering at a regular rate and its flowers have a remarkably high lasting quality as cut flowers in vase.

We claim:

1. A new and distinct variety of carnation plant, substantially as herein shown and described, characterized by its high productivity of well formed flowers of unusual color and exceptionally long lasting quality as cut flowers.

No references cited.

ROBERT E. BAGWILL, Primary Examiner